• (12) United States Patent
  Labarre et al.

(10) Patent No.: US 7,014,845 B1
(45) Date of Patent: Mar. 21, 2006

(54) CROSSLINKED COPOLYMERS BASED ON NON-CROSSLINKED POLYCARBOXYLIC COPOLYMERS

(75) Inventors: Denis Labarre, Villebon sur Yvette (FR); Nada Lambert, Paris (FR); Cathy Ducos, Anet (FR); François Diancourt, Epernon (FR)

(73) Assignee: Societe de Conseils de Recherches et d'Applications Scientifiques (S.C.R.A.S), (FR)

( * ) Notice: Subject to any disclaimer, the term of this patent is extended or adjusted under 35 U.S.C. 154(b) by 0 days.

(21) Appl. No.: 10/089,287

(22) PCT Filed: Oct. 3, 2000

(86) PCT No.: PCT/FR00/02731

§ 371 (c)(1),
(2), (4) Date: Mar. 26, 2002

(87) PCT Pub. No.: WO01/25295

PCT Pub. Date: Apr. 12, 2001

(30) Foreign Application Priority Data

Oct. 4, 1999 (FR) .................................. 99 12363

(51) Int. Cl.
*A61K 31/74* (2006.01)
*A61K 47/48* (2006.01)
*A61K 31/78* (2006.01)
*A61K 31/765* (2006.01)

(52) U.S. Cl. ............... 424/78.1; 424/78.08; 424/78.17; 424/78.1

(58) Field of Classification Search ............. 424/78.08, 424/78.17, 78.2, 78.1
See application file for complete search history.

(56) References Cited

U.S. PATENT DOCUMENTS 5,017,229 A   5/1991  Burns et al.
5,219,971 A * 6/1993  Heidel et al. ................ 527/314
6,229,009 B1 * 5/2001  Lambert et al. .......... 536/123.1

FOREIGN PATENT DOCUMENTS

WO      8601214       2/1986
WO      8902445       3/1989
WO      9116881       11/1991
WO      9808897       3/1998
WO   WO 98/08897   *  3/1998
WO      0027886       11/1999

* cited by examiner

*Primary Examiner*—Thurman K. Page
*Assistant Examiner*—Blessing Fubara
(74) *Attorney, Agent, or Firm*—Charles A. Muserlian

(57) ABSTRACT

The invention relates to cross-linked copolymers based on non cross-linked polycarboxylic copolymers, said non crosslinked copolymers containing at least one polysaccharide. The invention also relates to a process for the preparation of these copolymers and their use in particular as a support in pharmaceutical compositions.

23 Claims, No Drawings

CROSSLINKED COPOLYMERS BASED ON NON-CROSSLINKED POLYCARBOXYLIC COPOLYMERS

This application is a 371 of PCT/FR00/02731 filed Oct. 3, 2000.

The invention relates to cross-linked copolymers based on non cross-linked polycarboxylic copolymers, said non cross-linked copolymers containing at least one polysaccharide. The invention also relates to a process for the preparation of these copolymers and their use in particular as a support in pharmaceutical compositions.

A subject of the invention is therefore cross-linked copolymers based on non cross-linked polycarboxylic copolymers and a cross-linking agent comprising at least two amine functions; each non cross-linked polycarboxylic copolymer comprises at least one non cross-linked polysaccharide linked by a covalent bond to at least one other non saccharidic non cross-linked polymer. Finally at least one of the polysaccharides and non saccharidic polymers constituting the same non cross-linked copolymer, is polycarboxylic.

In Application WO98/08897, the Applicant claimed cross-linked copolymers, based on non cross-linked polycarboxylic polymers, said copolymers containing at least one polycarboxylic polysaccharide. Thus, a copolymer according to the aforementioned international Application contains at least one polycarboxylic polysaccharide and at least one other polycarboxylic polymer which is not a polysaccharide (lines 16–18 of Page 1 of Application WO98/08897). However, the process which consists of mixing the polycarboxylic polymers of the two types (polysaccharidic and non polysaccharidic), in aqueous solution does not exclude the existence, in the final cross-linked copolymer, of heterogeneities resulting from cross-linking reactions either between polysaccharides only, or between non polysaccharidic carboxylic polymers only.

The present Application therefore proposes to resolve this problem by firstly preparing copolymers of the two starting types (polycarboxylic polysaccharide polymer on the one hand and non-saccharidic polycarboxylic polymer on the other hand), then cross-linking the copolymers thus obtained; this allows possible heterogeneities to be excluded insofar as a covalent bond exists before the cross-linking reaction. The invention therefore proposes new cross-linked copolymers based on non cross-linked polycarboxylic copolymers.

The combination of a polysaccharide with another type of polymer allows modulation of the properties of the polysaccharides such as the hydrophily. Copolymers can thus be obtained with appropriate degradation properties as a function of their uses. Moreover, the copolymers according to the invention are advantageously prepared in aqueous medium.

According to the invention, the polysaccharide can be polycarboxylic or not. Similarly, the non saccharidic polymer can be polycarboxylic or not. If one of these two polymers is non polycarboxylic, the other is necessarily polycarboxylic in order to make cross-linking possible. The two saccharidic and non saccharidic polymers can both be polycarboxylic.

The non cross-linked non polycarboxylic polysaccharides can be chosen, for example, from agarose, agaropectin, amylose, amylopectin, arabinogalactan, carrageenans, cellulose or methylcellulose, chitosan, dextran, keratan sulphate, fucans and fucoidans, tragacanth, arabic, locust bean and guar gums or pullulan, or also their non carboxylic substituted derivatives.

The non cross-linked polycarboxylic polysaccharides can be chosen, for example, from glycosaminoglycanes, pectinic acid (pectin), alginic acid (alginate), the poly(sialic acids) such as colominic acid, xanthan, carboxylic derivatives of non carboxylic polysaccharides mentioned previously and in particular those of dextran such as carboxymethyldextrans and their derivatives, or also carboxylic derivatives of cellulose such as carboxymethylcelluloses. Among the glycosaminoglycanes, there can be mentioned hyaluronic acid and its derivatives, chondroitin sulphate, heparin, dermatan sulphate, heparan sulphate or a mixture of the latter.

Among the non saccharidic non cross-linked polycarboxylic polymers, there can be mentioned poly(glutamic acid), poly(aspartic acid), poly(maleic acid), poly(succinic acid), poly(itaconic acid), poly(malic acid) or poly(fumaric acid), polycarboxylic acrylic polymers such as poly(acrylic acid), poly(methacrylic acid) or copolymers of the latter such as Eudragits® L and S.

Among the non cross-linked and non saccharidic non polycarboxylic polymers, there can be mentioned poly(vinyl acetate), poly(vinyl alcohol), poly(acrylic esters), poly(methacrylic esters), poly(methacrylamides) and poly(acrylamides).

The expression saccharidic or non saccharidic polycarboxylic polymers, comprises polymers as defined above but also partially substituted derivatives of these polymers such as, for example, esters, amides and partially or totally substituted derivatives of these polymers such as the salts of these polycarboxylic polymers.

A more particular subject of the invention is cross-linked copolymers as defined above, characterized in that the polysaccharide is polycarboxylic. Preferably, it is chosen from pectinic acid (pectin), alginic acid (alginate), glycosaminoglycanes, and preferably hyaluronic acid, chondroitin sulphate, heparin, dermatan sulphate, heparan sulphate or a mixture of the latter.

A more particular subject of the invention is cross-linked copolymers as defined above, characterized in that the polysaccharide is non polycarboxylic. Preferably, it is chosen from agarose, agaropectin, amylose, amylopectin, arabinogalactan, carrageenans, cellulose or methylcellulose, chitosan, dextran, keratan sulphate, fucans and fucoidans, tragacanth, arabic, locust bean and guar gum or pullulan.

A more particular subject of the invention is cross-linked copolymers as defined above, characterized in that the non saccharidic non cross-linked polymer is polycarboxylic. Preferably, it is chosen from polycarboxylic acrylic polymers, and more particularly poly(acrylic acid) or poly(methacrylic acid).

A more particular subject of the invention is cross-linked copolymers as defined above, characterized in that the non saccharidic non cross-linked polymer is non polycarboxylic. Preferably, it is chosen from poly(vinyl acetate), poly(vinyl alcohol), poly(acrylic esters), poly(methacrylic esters), poly(methacrylamides) and poly(acrylamides).

The non cross-linked polycarboxylic copolymers according to the invention are linked together by a cross-linking agent. This cross-linking agent comprises at least two amine functions which are capable of reacting with the free carboxylic functions of said non cross-linked carboxylic copolymers. It can be chosen, for example, from proteins, polyamines, triamines, diamines, natural or synthetic amino acids, or derivatives of the compounds as defined above such as, for example, their salts, their esters or their amides. Among the amino acids, there can be mentioned, for example, arginine, lysine, histidine and ornithine. Among the diamines, there can be mentioned ethylenediamine, butanediamine, hexanediamine, heptanediamine, octanediamine or dodecanediamine. Among the polyamines, there can be mentioned chitosan, poly(ethylene imines), poly (amino acid) such as polylysine or polyornithine, as well as the copolymers of these polyamines. The cross-linking agent can also be chosen from compounds such as spermine, spermidine, melamine, guanidine or diethylenetriamine. A subject of the invention is also copolymers as defined above, in which the cross-linking agent is chosen from diamines, natural or synthetic amino acids or polyamines, and preferentially diamines. Preferably, the cross-linking agent used is a diamine and advantageously hexanediamine.

A more particular subject of the invention is also cross-linked copolymers as defined above, characterized in that the polysaccharide is a polysaccharide degradable by the microbial flora of the colon such as chondroitin sulphate, hyaluronic acid, pectinic acid, heparin, dextran, chitosan, amylose, pectin, alginates or xanthan, and more particularly chondroitin sulphate or chitosan.

A more particular subject of the invention is cross-linked copolymers as defined above, characterized in that the polysaccharide is chondroitin sulphate, the non saccharidic polymer is chosen from poly(acrylic acid) and poly(methacrylic acid), and the cross-linking agent is hexanediamine.

A subject of the invention is also a process for the preparation of cross-linked copolymers as defined above, said process characterized in that said non cross-linked polycarboxylic copolymers constituting the cross-linked copolymer is reacted in the presence of an activator and a cross-linking agent comprising at least two amine functions, in an appropriate reaction medium. Preferably, the preparation of cross-linked copolymers as defined above is carried out in an aqueous medium. The expression aqueous medium means a medium containing only water or water mixed with one or more solvents which are miscible with water such as, for example, acetone, lower alcohols such as ethanol, or acids. Other agents such as N-hydroxysuccinimide, which may encourage cross-linking, can also be used. Preferably the aqueous medium comprises only water. The implementation of the process according to the invention can be carried out in different ways by varying the order in which the different reagents are reacted. In fact, the process can consist of mixing together the non cross-linked polycarboxylic copolymers and the cross-linking agent, then adding the activator. The cross-linking process according to the invention can also consist of mixing together the non cross-linked polycarboxylic copolymers and the activator, then adding the cross-linking agent. The process can also consist of cross-linking one of the non cross-linked polycarboxylic copolymers constituting the cross-linked copolymer, by mixing said non cross-linked copolymer with the cross-linking agent then the activator or with the activator then the cross-linking agent, then adding to the reaction medium at least one other non cross-linked polycarboxylic copolymer, to cross-link it with said copolymer present in the reaction mixture. During the implementation of the process, the reagents introduced can first be solubilised in the reaction medium chosen. Preferably, the non cross-linked polycarboxylic copolymers and the cross-linking agent are mixed together in an aqueous medium until solubilisation then the activator is added. The process is implemented at a temperature comprised between −30 and 100° C., preferably between 0 and 40° C. and most preferentially at 4° C. The temperature at which the cross-linking process is implemented is of course lower than the degradation or decomposition temperatures of the reagents introduced.

The relative proportions of the reagents which are the non cross-linked polycarboxylic copolymers, the cross-linking agent and the activator can vary according to the characteristics of the sought copolymers. The non cross-linked polycarboxylic copolymers can vary in a molar ratio comprised between 0.01 and 100. The molar ratio of the cross-linking agent with respect to the total carboxylic functions can vary between 0.01 and 100. The molar ratio of the activator with respect to the total carboxylic functions can vary between 0.01 and 100.

The activator can be chosen from the coupling agents used in a standard fashion in peptide synthesis. Thus the activator can be chosen, for example, from carbodiimides, quinoline derivatives or mixed anhydrides. As examples of carbodiimides, there can be mentioned hydrohalides such as the hydrochloride of N-(3-dimethylaminopropyl)-N'-ethyl carbodiimide (EDC), N-cyclohexyl-N'-(2-morpholinoethyl) carbodiimide (CMC). As examples of quinoline derivatives, there can be mentioned 2-ethoxy-N-ethoxycarbonyl-1,2-dihydroquinoline (EEDQ), N-isobutoxycarbonyl-2-isobutoxy-1,2-dihydroquinoline (IIDQ), N-isobutoxycarbonyl-2-methoxy-1,2-dihydroquinoline (IMDQ), N-isobutoxycarbonyl-2-ethoxy-1,2-dihydroquinoline (IEDQ). As examples of mixed anhydrides, there can be mentioned chloroformates and more particularly isobutylchloroformate (IBC). Preferably, the activator used is N-(3-dimethylaminopropyl)-N'-ethyl carbodiimide hydrochloride. A subject of the invention is also a process for the preparation of cross-linked copolymers as defined above, in which the activator is chosen from carbodiimides, quinoline derivatives and mixed anhydrides.

The non cross-linked copolymers can be obtained for example by coupling corresponding polymers or by radical polymerisation from the polysaccharide and the monomer of the non saccharidic polymer.

A subject of the invention is also a process for the preparation of non cross-linked copolymers as defined above, said process characterized in that the monomer of the non saccharidic polymer is grafted onto the polysaccharide in an aqueous medium, under an inert atmosphere and in the presence of a catalyst, which monomer will then polymerize under these reaction conditions. The expression aqueous medium means a medium containing only water or water mixed with one or more solvents which are miscible with water such as, for example, acetone, lower alcohols such as ethanol or acids. The pH value of the reaction medium is adapted to the reagents used. The catalyst used is chosen from catalysts commonly used by a person skilled in the art such as for example ceric ions. The process is implemented at a temperature comprised between −30 and 100° C., preferably between 20 and 60° C. and most preferentially at 40° C. The temperature at which the process is implemented is of course lower than the degradation or decomposition temperatures of the reagents introduced.

The relative proportions of the reagents which are polysaccharides, monomers of non saccharidic polymers and the catalytic agent, can vary according to the characteristics of the sought cross-linked copolymers. The proportions of the reagents are defined as a function of the desired molecular masses of the non cross-linked polycarboxylic copolymers. The non cross-linked polymers can vary in a unit ratio comprised between 0.01 and 100 with respect to the saccharide units.

The cross-linked copolymers according to the invention can be used, for example, in the pharmaceutical, cosmetic, biomedical, veterinary, chemical, agrochemical or foodstuffs fields.

More particularly, a subject of the invention is a pharmaceutical composition containing at least one active ingredient and, as an inert support or an excipient, at least one cross-linked copolymer according to the invention. The expression active ingredient designates any substance or mixture of substances having a therapeutic activity.

Such a composition can be produced from these different components using any standard technique known to a person skilled in the art. It can be presented, for example, in the form of matrix tablets, tablets coated with copolymers of the present invention, multi-layer tablets, matrix pellets, pellets or microparticles coated with copolymers of the present invention. These microparticles and pellets may or may not be contained in capsules. It can also be presented in the form of microparticles or nanoparticles at least one constituent of which is a copolymer of the present invention or in any other form allowing oral administration. It can also be presented in any other form adapted to the chosen or appropriate administration mode such as suppositories or preparations for local application or injection. The quantity of active ingredient allowing an effective pharmacological action, in particular therapeutic, can vary as a function of the nature of the active ingredient, the age and/or the illness of the patient to be treated.

Thanks to its cross-linked network, a copolymer according to the invention can be used for sustained release of the active ingredient. A subject of the present invention is therefore also the use of a pharmaceutical composition according to the invention for the sustained release of one or more of the active ingredients that it contains.

Such compositions can also have other characteristics which optionally depend on the characteristics of the starting polymers such as bioadhesion. Thus, a pharmaceutical composition according to the invention can also be used as a bioadhesive pharmaceutical system. A subject of the present invention is therefore also the use of a pharmaceutical composition according to the invention as a bioadhesive system.

Compositions as defined above in which the polysaccharide is degraded by the flora of the colon, can also be used as a specific release system at the level of the colon by the action of the microbial flora. The concept of specific release at the level of the colon by the action of the microbial flora, is based on the property of the colon to possess a very abundant microbial flora which, moreover, has the potential to metabolize substances which are slightly degraded or not degraded by the upper part of the digestive tract. Such compositions are particularly suited for conveying active ingredients intended for the treatment of diseases of the colon, which allows their effectiveness to be increased and side effects to be reduced. These active ingredients include steroids such as dexamethasone and hydrocortisone, non-steroidal anti-inflammatories such as 5-aminosalicylic acid, antineoplastics such as methotrexate, tamoxifen, antispasmodics and chemotherapy agents. Such compositions are also particularly suited for conveying active ingredients which are absorbed more effectively at the level of the colon such as steroids or xanthine. Their direct administration at the level of the colon allows their effectiveness to be increased. Such compositions are also particularly suited for conveying active ingredients which are degraded in the upper parts of the digestive tract. Among these active ingredients, there can be mentioned peptides and proteins of natural or synthetic origin as well as pharmacologically active fragments such as oral vaccines, insulin, contraceptive peptides, plasminogen activator peptides, growth peptides and other peptides involved in hormonal regulation.

The following examples are presented in order to illustrate the above procedures and should in no event be considered as a limit to the scope of the invention.

EXPERIMENTAL PART

Synthesis of Non Cross-Linked Copolymers

Example 1

Synthesis of a Chondroitin Sulphate-Co-Polymethacrylic Acid Copolymer 250 mg of chondroitin sulphate (CS) in 50 ml of a previously degassed 0.2 M solution of $HNO_3$ is dissolved at 40° C. in a stoppered Erlenmeyer flask. 3.625 ml of a solution of cerium ions (concentration $8.10^{-2}$ mole/liter in $HNO_3$ 0.2 M previously degassed) and 2.5 ml of methacrylic acid are added. The reaction is carried out at 40° C. for approximately 50 minutes under stirring. After cooling down, the pH is adjusted to 7 using soda. A 1M citrate solution is added. The final medium is then filtered on a membrane with a 10 kilo-dalton pore size by tangential diafiltration. Analysis of the purified copolymer can be carried out on the solution thus obtained or after a lyophilization stage.

The molecular weight of the copolymer is measured by gel-permeation chromatography in the aqueous phase (medium NaCl 0.2 N). The columns are calibrated with dextran standards with molecular weights comprised between 40 000 and 400 000.

The weights are expressed as mean molecular weights by weight (Mw) and molecular weight at the chromatogram peak, representing the majority of the macromolecular population (Mp). The polydispersity index (Ip), corresponding to the ratio Mw/Mn (number-average molecular weight), represents the dispersion of the weights over the copolymer assembly.

Copolymer 1:
  Mw=170 000
  Mp=78 000
  Ip=5.38

The number of carboxyl groups present is determined by conductimetric assay. The copolymer solution to be assayed is first eluted on an ion exchange resin of sulphonic type (DOWEX 50Wx8). This preparative stage allows copolymers to be obtained in acid form and allows all the sulphate and carboxylate acidities of polysaccharidic origin to be assayed distinctly as well as the carboxylate acidities of non saccharidic carboxylic origin. Neutralisation of the solution by 0.1N soda is then followed by conductimetry. The results are expressed in meq NaOH (mg of NaOH/g of copolymers).

Copolymer 1:
  $-1.39.10^{+2}$ meq NaOH (PMA+CS),
  $-8.94.10^{+1}$ meq NaOH (PMA);
  $-5.08.10^{+1}$ meq NaOH(CS).

The NMR-$^{13}$C spectrum of the copolymer (PMA+CS) comprises the peaks characteristic of CS and PMA, namely respectively the multiplet between 51 and 105 ppm corresponding to the carbons carried by the glucuronics and galactosamine, the peak characteristic of N-acetyl centred at 175 ppm, and the signals corresponding to the methyls (19.2 ppm) and to the carboxyls (186.4 ppm) of polymethacrylic acid. But this spectrum also comprises signals which belong to neither of the two entities (119.8 and 181.4 ppm) and which are attributed to the bonds between the CS and the PMA. This analysis demonstrates the polymerisation of the methacrylic acid on the CS.

Example 2

Synthesis of Chondroitin Sulphate-Co-Polymethacrylic Acid Copolymers with Variable Molecular Weights and CS/PMA Ratios Different molecular weights and CS/PMA ratios can be obtained by modifying the proportions of the reagents introduced and in particular by:
- modifying the quantity of cerium.
- modifying the quantity of methacrylic acid
- modifying the molarity of the nitric acid solution.

These studies show significant differences in weight between the synthesized polymers (GPC data).

250 mg of chondroitin sulphate is dissolved at 40° C. in 50 ml of a previously degassed X M solution of $HNO_3$ in a stoppered Erlenmeyer flask. Y ml of a solution of cerium ions (concentration $8.10^{-2}$ mole/liter in previously degassed $HNO_3$ X M) and Z ml of methacrylic acid are added. The reaction is carried out at 40° C. for approximately 50 minutes under stirring. After cooling down, the pH is adjusted to 7 using soda. A 1M citrate solution is added. The final medium is then filtered on a membrane with a pore size of 10 kilo-daltons by tangential diafiltration.

Analysis of the purified copolymer can be carried out on the solution thus obtained or after a lyophilization stage.

The operating conditions as well as the molecular weight of the purified copolymers (determined by aqueous gel-permeation chromatography) are set out in Table 1 below.

Cross-Linking of the Synthesized Copolymers

Example 3

100 mg of the copolymer obtained in Example 1, diaminohexane and N-hydroxysuccinimide are dissolved in 2 ml of an aqueous solution containing triethylamine in order to obtain a final pH of 8.5–9.5. EDC is added. The pH is maintained at 8.5–9.5 for 24 hours at 4° C. The precipitates obtained are washed with 5 M NaCl solutions then with bidistilled water. The precipitates are then lyophilised and the weight is then determined.

The quantities of diaminohexane, EDC and N-hydroxysuccinimide studied are as follows:

| Preparation | A | B | C |
| --- | --- | --- | --- |
| EDC (mg) | 320 | 170 | 170 |
| diaminohexane (mg) | 160 | 160 | 80 |
| hydroxysuccinimide (mg) | 310 | 310 | 155 |
| Weight of precipitate (mg) | 180 | 17 | 80 |

Example 4

100 mg of the copolymer obtained in Example 1, 160 mg of diaminohexane and 310 mg of N-hydroxysuccinimide are dissolved at 4° C. in 2 ml of borate buffer at pH9. 320 mg of EDC is added. The reaction is carried out at 4° C. for 24 hours under stirring. The precipitates obtained are washed with 5 M NaCl solutions then with bidistilled water. Then the precipitates are lyophilized. The weight of the precipitates obtained is 100 mg.

Example 5

100 mg of the copolymer obtained in Example 1, 160 mg of diaminohexane and 310 mg of N-hydroxysuccinimide are dissolved at 4° C. in 2 ml of bicarbonate buffer at pH 9. 320 mg of EDC is added. The reaction is carried out at 4° C. for 24 hours under stirring. The precipitates obtained are washed with 5 M NaCl solutions then with bidistilled water. Then the precipitates are lyophilized. The weight of the precipitates obtained is 50 mg.

TABLE 1

| concentration of $HNO_3$ = X | concentration of cerium = Y | volume of MA = Z | molecular weight |
| --- | --- | --- | --- |
| 0.2 M | $5.5 \cdot 10^{-3}$ M | 0.1 ml | Mp = 70 000<br>Mw = 138 000<br>Ip = 3 |
| 0.2 M | $1.1 \cdot 10^{-2}$ M | 0.1 ml | Mp = 48 000<br>Mw = 81 000<br>Ip = 3 |
| 0.2 M | $1.7 \cdot 10^{-2}$ M | 0.1 ml | Mp = 31 000<br>Mw = 48 000<br>Ip = 3 |
| Variation in $HNO_3$ concentration | | | |
| 0.05 M | $5.5 \cdot 10^{-3}$ M | 0.5 ml | Mp = 79 000<br>Mw = 194 000<br>Ip = 3.29 |
| 0.05 M | $5.5 \cdot 10^{-3}$ M | 1.25 ml | Mp = 225 000<br>Mw = 245 000<br>Ip = 13.99 |
| 0.05 M | $5.5 \cdot 10^{-3}$ M | 2.5 ml | Mp =<br>Mw = >standard<br>Ip = |
| 0.1 M | $5.5 \cdot 10^{-3}$ M | 0.5 ml | Mp = 69 000<br>Mw = 147 000<br>Ip = 3.17 |
| 0.1 M | $5.5 \cdot 10^{-3}$ M | 1.25 ml | Mp = 80 000<br>Mw = 180 000<br>Ip = 3.58 |
| 0.1 M | $5.5 \cdot 10^{-3}$ M | 2.5 ml | Mp = 77 000<br>Mw = 140 000<br>Ip = 3.60 |
| 0.2 M | $5.5 \cdot 10^{-3}$ M | 0.5 ml | Mp = 61 000<br>Mw = 160 000<br>Ip = 3.49 |
| 0.2 M | $5.5 \cdot 10^{-3}$ M | 1.25 ml | Mp = 80 000<br>Mw = 190 000<br>Ip = 2.94 |
| 0.2 M | $5.5 \cdot 10^{-3}$ M | 2.5 ml | Mp = 80 000<br>Mw = 170 000<br>Ip = 2.72 |

The invention claimed is:

1. A cross-linked copolymer prepared from a reaction between at least one non-cross-linked polysaccharide and at least one non-polysaccharide non-cross-linked polymer to link the two by a covalent bond to form a non-cross-linked polycarboxylic copolymer and reacting the latter with a cross-linking agent selected from the group consisting of diamines, natural and synthetic amino acids and polyamides to form a cross-linked copolymer, at least one of the polysaccharides or non-cross-linked polymer being polycarboxylic.

2. A copolymer of claim 1, wherein the polysaccharide is non-polycarboxylic.

3. A copolymer of claim 2 wherein the non-cross-linked non-polycarboxylic polysaccharide is selected from the group consisting of agarose, agaropectin, amylose, amylopectin, arabinogalactan, carrageenans, cellulose, methylcellulose, chitosan, dextran, keratan sulfate, fucans and fucoidans, tragacanth, arabic, locust bean, guar gums and pullulan.

4. A copolymer of claim 1 wherein the polysaccharide is polycarboxylic.

5. A copolymer of claim 4 wherein the polycarboxylic polysaccharide is selected from the group consisting of glycosaminoglycanes, pectinic and alginic acid.

6. A copolymer of claim 4 wherein the polycarboxylic polysaccharide is glycosaminoglycane selected from the group consisting of hyaluronic acid, chondroitin sulfate, heparin, dermatan sulfate and heparin sulfate.

7. A copolymer of claim 1 wherein the non-saccharidic polymer is non-polycarboxylic.

8. A copolymer of claim 7 wherein the non-polycarboxylic non-saccharidic polymer is selected from the group consisting of poly(vinyl acetate), poly(vinyl alcohol), poly(acrylic esters), poly(methacrylic esters), poly(methacrylamines) and poly(acrylamides).

9. A copolymer of claim 1 wherein the non-saccharidic polymer is polycarboxylic.

10. A copolymer of claim 9 wherein the non-saccharidic polymer is a polycarboxylic acrylic polymer.

11. A copolymer of claim 10 wherein the polycarboxylic acrylic polymer is poly(acrylic acid) or poly(methacrylic acid).

12. A copolymer of claim 1 wherein the cross-linking agent is a diamine.

13. A copolymer of claim 1 wherein the polysaccharide is degradable by the microbial flora of the colon.

14. A copolymer of claim 13 wherein the polysaccharide is selected from the group consisting of chondroitin sulfate, hyaluronic acid, pectinic acid, heparin, dextran, chitosan, amylose, pectin, alginates and xanthan.

15. A copolymer of claim 14 wherein the polysaccharide is chondroitin sulfate, and the non-saccharidic polymer is poly(acrylic acid) or poly(metharylic acid), and the cross-linking agent is hexanediamine.

16. A process for the preparation of cross-linked copolymers of claim 1 comprising reacting said two separate non-cross-linked polycarboxylic copolymers in an aqueous medium in the presence of an activator of said cross-linking agent.

17. The process of claim 16 wherein the activator is selected from the group consisting of carbodiimides, quinoline derivatives and mixed anhydrides.

18. A process for the preparation of non-cross-linked copolymers of claim 1, comprising grafting the monomer of the non-saccharidic polymer onto the polysaccharide in an aqueous medium, under an inert atmosphere and in the presence of a catalyst which monomer will then polymerize under these reaction conditions.

19. A pharmaceutical composition containing at least one active ingredient and, as in inert support or excipient, at least one cross-linked copolymer of claim 1.

20. A pharmaceutical composition containing at least one active ingredient and, as an inert support or excipient, at least one copolymer of claim 13.

21. A method of treating a disease of the colon in warm-blooded animals comprising administering to warm-blooded animals in need thereof an effective amount of an active colon treating ingredient with an excipient of at least one copolymer of claim 1 for sustained release.

22. The method of claim 21 wherein the active ingredient is absorbed at the colon level.

23. The method of claim 21 wherein the active ingredient is released in the upper parts of the digestive tract.

* * * * *